United States Patent
Torcia

(10) Patent No.: US 6,572,866 B1
(45) Date of Patent: Jun. 3, 2003

(54) NERVE GROWTH FACTOR AS A VACCINE ADJUVANT

(75) Inventor: Maria Torcia, Florence (IT)

(73) Assignee: Protechtion Unlimited, Inc., Wilmington, DE (US)

( * ) Notice: Subject to any disclaimer, the term of this patent is extended or adjusted under 35 U.S.C. 154(b) by 0 days.

(21) Appl. No.: 09/269,883

(22) PCT Filed: Apr. 30, 1998

(86) PCT No.: PCT/US98/08652

§ 371 (c)(1),
(2), (4) Date: Jun. 1, 1999

(87) PCT Pub. No.: WO98/48832

PCT Pub. Date: Nov. 5, 1998

Related U.S. Application Data

(63) Continuation-in-part of application No. PCT/US98/08652, filed on Apr. 30, 1998, and a continuation-in-part of application No. 08/847,228, filed on May 1, 1997, now abandoned.

(51) Int. Cl.$^7$ .......................... A61K 47/42; A61K 39/39
(52) U.S. Cl. ........................ 424/278.1; 424/184.1; 424/198.1; 514/2; 514/12
(58) Field of Search .................. 514/2, 12; 424/184.1, 424/278.1, 198.1

(56) References Cited

PUBLICATIONS

Paul, William E. "Fundamental Immunology", 3rd ed., Raven Press, New York, pp. 1353–1369, 1993.*

Thorpe et al., "Mechanisms of lymphocyte activation by nerve growth factor", Ann. N.Y. Acad. Of Sci., 1990, vol. 594, pp. 78–84.

Brodie et al., "Functional nerve growth factor receptors on human B lymphocytes. Interaction with IL–2", Immunol., Jun. 1, 1992, vol. 148, No. 11, pp. 3492–3497.

Melamed et al., "Nerve growth factor signal transduction in human B lymphocytes is mediated by gp 140trk", Eur. J. Immunol., Sep. 1996, vol. 26, pp. 1985–1992.

Richard J. Hodes, Aging and the immune system, Immunological Reviews, 160:5–8 (1997).

Maria Torcia et al., "Nerve Growth Factor Is an Autocrine Survival Factor for Memory B Lymphocytes", Cell, vol. 85, May 3, 1996, pp. 345–356.

Eisen, Immunology An Introduction to Molecular and Cellular Principle of the Immune Responses, 2nd Ed., Harper & Row, Philadelphia, p. 447, 1980.

Kimball, Introduction to Immunology, 3rd Ed., Macmillan Publishing Company, New York, p. 453–457, 1990.

* cited by examiner

*Primary Examiner*—Gary Kunz
*Assistant Examiner*—Stephen Gucker
(74) *Attorney, Agent, or Firm*—Rothwell, Figg, Ernst & Manbeck

(57) ABSTRACT

A vaccination method utilizes a pharmaceutical combination for enhancing vaccine effectiveness. The method utilizes an immune response-triggering vaccine capable of stimulating production in an immunodeficient animal antibodies to a disease-causing agent foreign to the animal. As an adjuvant, a vaccine effectiveness-enhancing amount of Nerve Growth Factor (NGF) is administered, which enhances production and affinity of the antibodies in the animal, in response to the vaccine.

19 Claims, 2 Drawing Sheets

SUBSTITUTE SHEET (RULE 26)

NERVE GROWTH FACTOR AS A VACCINE ADJUVANT

CROSS-REFERENCE TO RELATED APPLICATIONS

The present application is a continuation-in-part of International Application No. PCT/US98/08652, filed Apr. 30, 1998, and is a continuation-in-part of U.S. Ser. No. 08/847,228, filed May 1, 1997, now abandoned.

FIELD OF THE INVENTION

The present invention relates to the field of vaccines.

DESCRIPTION OF THE BACKGROUND ART

Humans livestock and pets often are vaccinated to prevent disease, or reduce the severity of disease. Vaccination results in the production of antibodies, which are serum proteins capable of binding specifically to antigen substances used in the vaccine. This humoral response involves the selection of specific lines of B lymphocytes, and the proliferation and differentiation of the selected cells to yield clones of antibody-producing plasma cells.

Antibody production reaches a peak within several weeks after immunization, and then gradually declines. Because of a constant turnover of serum proteins, the decline in antibody production is accompanied by a corresponding decline in the circulating level of antibodies. However, if the patient is challenged again with the same antigen, a new response curve is initiated more rapidly and more intensely than the first one. This is called a secondary, booster, or anamnestic response, and in healthy patients results in much higher antibody levels with higher affinity to the antigen than the first exposure, or primary immunization. The increased rate of antibody synthesis is the result of an increased number of antibody producing plasma cells. These cells are scarce in the lymph nodes of the unimmunized patient, which contain mostly small lymphocytes. However, in healthy patients, plasma cells constitute up to 3% of the total lymph node cells after a primary immunization, and as much as 30% of the lymph node cells after a secondary immunization.

The secondary response is said to be due to immunological memory. That is, the healthy organism is able to "remember" its prior exposure to the antigen, and react more promptly and efficiently the second time it is exposed, even if the amount of specific antibodies in the serum has declined to a very low level in the meantime.

Certain conditions such as aging, malnutrition, drug addiction, alcoholism, and certain disease states such as diabetes and AIDS, lead to immunodeficiency, in which many immune responses are quenched and vaccination is of reduced effectiveness. There thus remains a need in the art for improved vaccination techniques, particularly among the elderly or otherwise immunodeficient.

SUMMARY OF THE INVENTION

In accordance with the present invention, a vaccination method utilizes a pharmaceutical combination for enhancing vaccine effectiveness. The pharmaceutical combination comprises an immune response-triggering vaccine capable of stimulating production in an immunodeficient animal of antibodies to a disease-causing agent foreign to said animal. The pharmaceutical combination further includes a vaccine effectiveness-enhancing amount of Nerve Growth Factor (NGF), which enhances production and affinity of said antibodies in said animal, in response to said vaccine. The vaccine and the NGF can be administered separately or together. In a preferred method, the vaccination method comprises administering to an immunodeficient animal a first dose of an immune response-triggering vaccine capable of stimulating production in an animal of antibodies to a disease-causing agent foreign to said animal; then, within a time period of between about 1 week and about 2 months after administration of said first dose, administering to said animal either 1) a vaccine effectiveness-enhancing amount of Nerve Growth Factor (NGF) which enhances production of said antibodies in said animal in response to said vaccine or 2) booster dose of said vaccine, along with a vaccine effectiveness-enhancing amount of said Nerve Growth Factor (NGF), so as to enhance effectiveness of said vaccine in said animal.

DETAILED DESCRIPTION OF THE PREFERRED EMBODIMENTS

Figure 1:
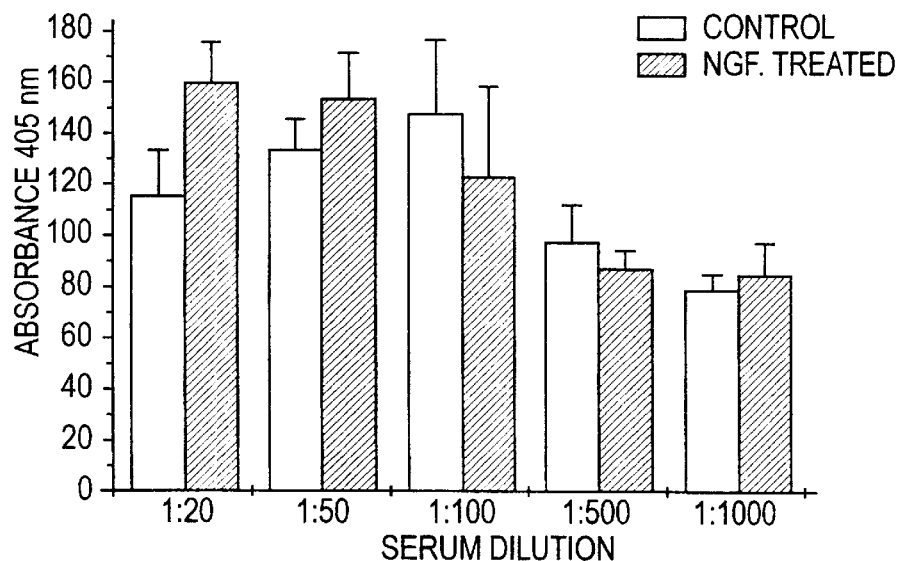
FIG. 1 is a graph showing production of antibodies in adult mice treated in accordance with the invention, as compared to control.

It has unexpectedly been discovered that Nerve Growth Factor not only acts on nervous system development, but has an important role in the immune system physiology. Memory B cells, lymphocytes that keep trace (memory) of an organism's encounter with a given chemical structure (antigen), produce and secrete NGF, bind it through cell surface receptors, and respond to its biologic message (autocrine circuit of production and response by the same cell), remaining alive for many years, or even throughout the life of the organism, at variance with the rest of lymphoid cells that have a much shorter life span.

Without being bound to any particular theory, it is believed that, beyond the activity of NGF in maintaining survival of memory B cells, NGF might also influence their generation, positively acting on their precursors. The memory cell could originate from the ability of producing NGF, stochastically acquired by a progenitor otherwise destined to death by apoptosis (suicide), which would give rise to the autocrine loop sustaining differentiation to the stage of mature memory cell, and than survival of the latter. Thus, administration of exogenous NGF to animals gives rise to higher numbers of memory cells. A larger pool of memory cells provides the individual with a stronger and more durable protection against the antigen. This improvement is more evident in conditions of immunodeficiency, e.g., aging, in which many immune responses are quenched. By increasing the number of memory B cells, NGF improves the ability of the immune system to recognize antigen at a very low concentration, because of the higher affinity of surface antibodies on the memory B cells.

The present invention is applicable to animals capable of forming antibodies in an immune reaction, such as mammals including humans, livestock and pets, as well as birds such as domesticated fowl.

As persons age, their immune response is reduced, and vaccination effectiveness diminished due to the prevalance of low affinity antibody response. Accordingly, the invention is particularly applicable for use with humans over the age of 45, particularly those age 50 and above.

The invention is also applicable to transplant patients who are immunodeficient as a result of administration of anti-rejection drugs such as cyclosporin.

It is believed that the present invention is applicable to any known vaccine, examples of which include Influenza vaccine, Hemophilus influenzae vaccine, Hepatitis A virus vaccine, Hepatitis B virus vaccine, Hepatitis C virus vaccine, Tuberculosis vaccine, Herpes-Zoster virus vaccine, Cytomegalovirus vaccine, Pneumococcal pneumonia vaccine, Meningococcal meningitis vaccine, Diphtheria vaccine, Tetanus vaccine, Rabies vaccine, Helicobacter pylori vaccine, polio vaccine and smallpox vaccine.

It also is believed that the invention is applicable to any future vaccine, such as a vaccine which may be developed for vaccination against the AIDS virus.

Generally, vaccines are administered in amounts within the range of from about $1 \times 10^{-9}$ g to about $1 \times 10^{-3}$ g, and more typically withing the range from about $1 \times 10_{-8}$ g to about $1 \times 10^{-4}$ g.

Vaccine effectiveness-enhancing amounts of NGF generally are administered in amounts within the range of about 0.001–100 mg/kg body weight of the recipient, preferably in amounts of about 0.1–10 mg/kg, and more preferably about 0.3–3 mg/kg.

In accordance with one aspect of the present invention, the NGF can be administered before and/or concurrently with administration of the vaccine.

The present invention is particularly effective when administered in connection with a secondary (booster) vaccination dose. Secondary or booster vaccination doses typically are administered within a time period of about 1 week to about 2 months after administration of the first (primary) vaccine dose, preferably within about 10–45 days of the first vaccine dose, more preferably within about 10–30 days of administration of the first vaccine dose, and according to some embodiments within about 10–20 days of administration of the first vaccine dose.

In accordance with one embodiment, a dose of NGF is administered to a recipient several days prior to administration of a secondary (booster) vaccine dose, most preferably about 3–4 days prior to administration of the secondary (booster) vaccine dose. In particularly preferred embodiments, NGF also is administered concurrently with administration of the secondary (booster) vaccine dose.

Administration of the NGF and vaccine may take place by any suitable means, such as injection, infusion or orally. In particularly preferred embodiments, administration is by injection.

In accordance with one embodiment, NGF can be administered by introducing into a recipient myoblasts including a vector carrying a gene coding for NGF. In accordance with this embodiment, NGF is produced by the myoblasts in the recipient to enhance immune system effectiveness.

When a vaccine and NGF are administered concurrently, they can be provided as a single composition including the vaccine and NGF.

Compositions including a vaccine and/or NGF can also include one or more pharmaceutically acceptable carriers and optionally other therapeutic ingredients.

Formulations suitable for injection or infusion include aqueous and non-aqueous sterile injection solutions which may optionally contain antioxidants, buffers, bacteriostats and solutes which render the formulations isotonic with the blood of the intended recipient, and aqueous and non-aqueous sterile suspensions which may include suspending agents and thickening agents. The formulations may be presented in unit-dose or multi-dose containers, for example, sealed ampules and viles, and may be stored in a freeze-dried (lyophilized) condition requiring only the addition of the sterile liquid carrier, for example, water for injection, immediately prior to use.

The NGF utilized preferably is matched to the recipient, e.g., human NGF preferably is utilized with human recipient. The present invention is applicable to native (i.e., naturally occurring) NGF, as well as synthetic NGF and recombinant NGF corresponding to native NGF, having the amino acid sequence of native NGF, biologically active amino acid sequences substantially similar thereto, or an abbreviated sequence form thereof, and their biologically active analogs, having substituted, deleted, elongated, replaced, or otherwise modified sequences which possess bioactivity substantially similar to that of NGF.

The invention is further illustrated by the following examples which are not intended to be limiting.

Aging is an art-recognized cause of immunodeficiency. "One widely observed change in the in vivo immune response of aged humans or experimental animals is the diminished ability to generate high affinity protective antibody responses to immunization against infectious agents or experimental antigens. Hodes, R. J., *Immunological Reviews* 160:5–8 (1997). In certain of the following examples, "normal" mice are immunocompetant control animals (less than 5 months old) against which aged mice (greater than 5 months old) were tested to demonstrate efficacy of the present invention.

Immunocompetence as a function of age is expressed in the general population of both mice and men according to a Gaussian. distribution mode. This is clearly evident from the experimental data provided below, whereby the titer of anti-NIP antibodies is significantly lower in mice aged five months or more than in younger, fully immunocompetent mice. The fact that reconstitution of immunological parameters was observed in the experimental systems presented below demonstrates NGF efficacy.

From an immunological standpoint, mice begin aging from the fifth month of life in a corresponding way as humans do from the age of approximately 40 years, and the process goes on with progressive intensity. The above holds true for substantially every mammal, and in each species a threshold age can be determined, in which immunodeficiency starts to be evident in a significant number of individuals. According to the above considerations on the Gaussian distribution mode, the later number will be progressively higher as the value of the threshold age increases. The above-cited Hodes reference states that "[o]ne of the most consistent changes noted in the T cells of aging humans and mice is the progressive shift from a predominance of naive to memory cells within the CD4+population," providing clear evidence that the results achieved with the present invention in mice can be extrapolated to humans.

EXAMPLE 1

Two groups of ten aged (>5 months old) C57/BL6 female mice were immunized i.p. with 0.1 mg per mouse of ($^4$-Hydroxy-5-iodo-3-nitro-phenyl)acetyl-bovine serum albumin (NIP-BSA) (Reth et al, 1978) in 0.1 ml phosphate-buffered saline (PBS) resuspended in 0.1 ml complete Freund's adjuvant. After 21 days, animals in one group were injected with 50 μg per animal of mouse Nerve Growth Factor (NGF), purified from submandibular salivar glands as described, whereas animals in the other group were treated with the same amount of purified NGF, previously inactivated by heating (72° C. for 20 minutes). After an additional four days, animals in the two groups were given the same NGF treatment as above, and all mice were boosted with 0.1 mg NIP-BSA in incomplete Freund's adjuvant. After four days, ≈0.4 ml of blood were obtained from each animal by retroorbital plexus aspiration, and the anti-BSA antibodies were neutralized by addition of BSA to the serum samples. NIP-specific IgG titer was then assessed in ELISA. Plates were coated with NIP-BSA (35 μg/ml in PBS), and, after saturation with PBS containing 1% BSA and rinsing with PBS with 0.05% (v/v) Tween-20, coated wells were incubated for 1 hour at 37° C. with serial dilution of mouse sera; a pool of pre-immune mouse sera was used as negative control. Bound Ig were detected by addition of alkaline phosphatase-conjugated goat anti-mouse IgG. The final reaction was visualized by incubating with NPP (Sigma) substrate solution, and absorbance at 405 nm was recorded. Results are shown in Table A below, and in FIGS. 1 and 2.

TABLE A

Titer of NIP-specific IgG ($Abs_{405}$ arbitrary units) in mice sera

| Serum dilution | NGF-treated | Controls | Significance level (p) |
| --- | --- | --- | --- |
| Aged 1:20 | 179.1 ± 29.3 | 82.6 ± 18.3 | <0.05 |
| Normal 1:20 | 159.9 ± 15.8 | 116.7 ± 17.0 | n.s.s. |
| Aged 1:50 | 146.3 ± 3.0 | 18.6 ± 6.3 | <0.001 |
| Normal 1:50 | 153.7 ± 19.2 | 133.8 ± 11.9 | n.s.s. |
| Aged 1:100 | 97.3 ± 17.5 | <10 | <0.0001 |
| Normal 1:100 | 123.8 ± 34.7 | 148.4 ± 28.6 | n.s.s. |
| Aged 1:500 | 75.5 ± 2.6 | <10 | <0.0001 |
| Normal 1:500 | 87.3 ± 7.53 | 98.2 ± 14.2 | n.s.s. |
| Aged 1:1,000 | 80.1 ± 11.2 | <10 | <0.0001 |
| Normal 1:1,000 | 84.2 ± 12.3 | 78.4 ± 6.3 | n.s.s. |

Figure 2:
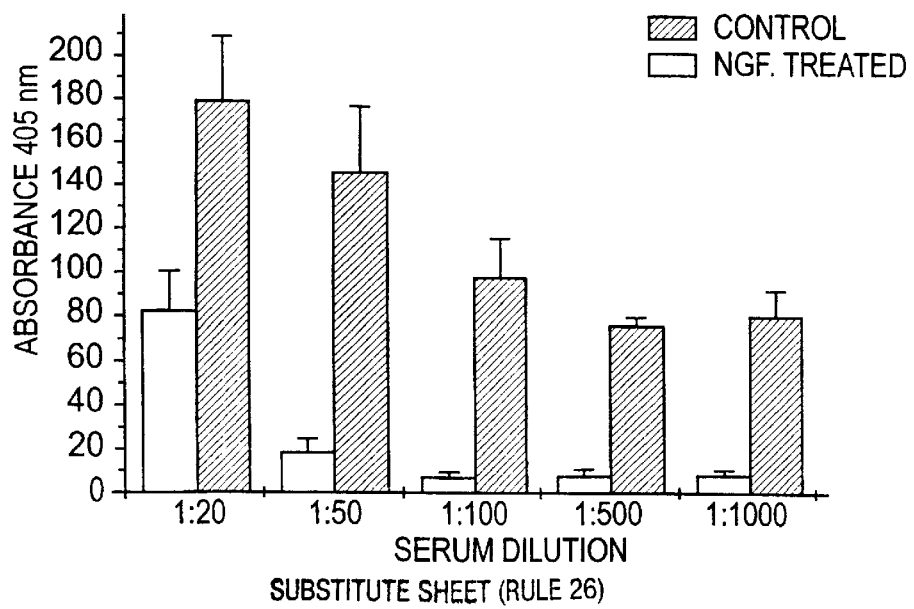
FIG. 2 is a graph showing enhanced production of antibodies in aged mice utilizing the present invention, as compared to control.

FIGS. 1 and 2 show that NGF treatment dramatically increase the titer of serum NIP-specific IgG in aged mice, while it does not affect the response in young mice.

The affinity for the antigenic determinant (NIP-BSA) of the specific IgG produced in NGF-treated and in control mice was analyzed on a BIAcore machine, by using NIP-BSA coupled to dextran as a sensor chip. The results of these experiments indicate that the IgG affinity for the antigen is much lower in elderly mice than in young mice, indicating a defect in the maturation of memory cells. However NGF treatment in elderly mice is able to restore the production of high affinity IgG, thus modifying not only the quantity but also the quality of the humoral immune response (data not shown).

Figure 4:
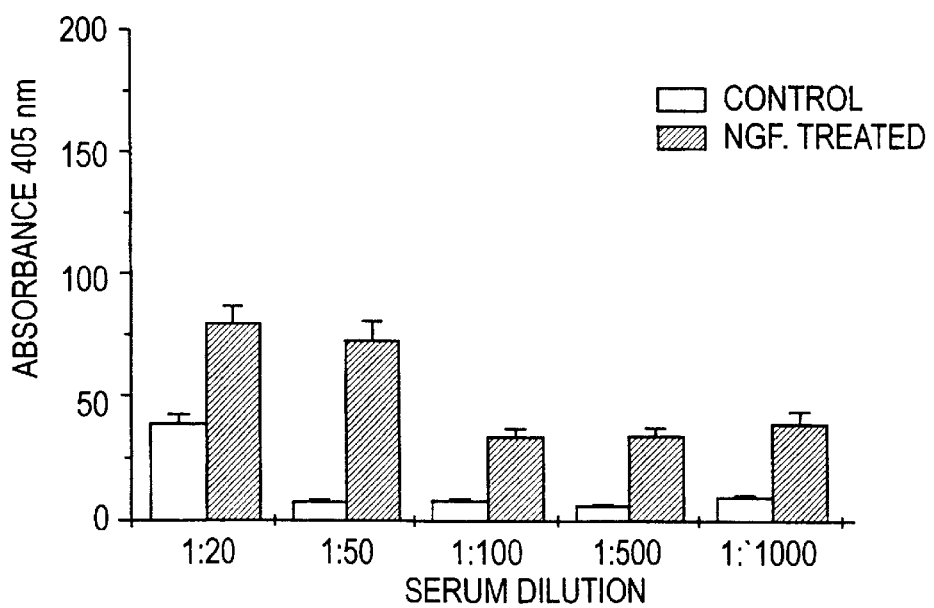
FIG. 4 is a graph showing enhanced production of antibodies in aged mice in accordance with the present invention, after three months from immunization, as compared to control.

In order to ascertain whether this simple NGF administration schedule was able to maintain a high titer of specific IgG for a long period after immunization, we obtained blood samples from the same group of aged immunized mice three months after the boost with NIP-BAS. The serum titer of NIP-specific IgG was measured by ELISA. FIG. 4 shows that the group of NGF-treated animals maintained a significant titer of NIP-specific IgG even after a long period from the boost immunization.

Overall, these results indicate that the quality and quantity of humoral immune response in aged mice can be corrected by even a single NGF administration at the end of the primary response, when it is known that maturation of memory B cells occurs. NGF treatment, at this time, increase the survival of memory B cells that, in aged mice, are not able to produce by themselves the cytokine. In contrast, NGF treatment is ineffective in normal young animals, whose memory lymphocytes are able to produce sufficient amounts of NGF and, thus, to survive. Furthermore, the data suggest that NGF administration might be helpful in almost all of the primary or secondary immunodeficiency conditions characterized by an impaired humoral immune response (cancer, AIDS, chronic inflammation, etc.).

The invention is further supported by Example 2 as follows.

EXAMPLE 2

Summary

Production of Nerve Growth Factor (NGF) was assessed in cultures of human T and B lymphocytes and macrophages. NGF was constitutively produced by B cells only, which also expressed surface $p140^{trk-A}$ and $p75^{NGFR}$ molecules, and hence efficiently bound and internalized the cytokine. Neutralization of endogenous NGF caused disappearance of bcl-2 protein and apoptotic death of resting lymphocytes bearing surface IgG or IgA, a population comprising memory cells, while surface IgM/IgD "virgin" B lymphocytes were not affected. In vivo administration of neutralizing anti-NGF antibodies caused strong reduction in the titer of specific IgG in mice immunized with tetanus toxoid, nitrophenol, or arsenate, and reduced numbers of surface IgG or IgA B lymphocytes. Thus, NGF is an autocrine survival factor for memory B lymphocytes.

Introduction

Nerve Growth Factor (NGF), described and characterized almost thirty years ago (Levi-Montalcini, 1987; Cohen, 1960) as the first soluble signal mediating intercellular communications, is a member of the family of proteins known as neurotrophins, which are critical for regulated development and survival of neuronal cells (Barde, 1990). Its role in maintaining survival of neurons from sympathetic and sensory ganglia has been established for decades (Levi-Montalcini and Angeletti, 1966, 1968). In recent years, these initial observations have been extended to other populations of central nervous system neurons, including basal forebrain cholinergic cells (Johnson et al., 1986; Shelton and Reichardt, 1986). It is believed that NGF, like the other neurotrophins, is produced in the nervous system by accessory cells, such as glial cells and oligodendrocytes (Ernfors et al., 1990, Hofer et al., 1990), which therefore regulate the differentiation process of neurons mostly through the formation of paracrine circuits.

The neurotrophins, including NGF, brain-derived neurotrophic factor (BDNF), neurotrophin-3 (NT-3), and NT4/5, exert their effects on cellular targets via specific surface receptors which, upon binding and internalization of the ligand, trigger a cascade of biochemical events, representing the adaptive response (reviewed in Barde, 1990). Two classes of neurotrophin binding sites can be identified on target cells, based on low ($K_d$ 1 nM) and high ($K_d$ 20 pM) affinity for the ligand(s). The molecular nature of these receptors has been recently characterized (Meakin and Shooter, 1992). A 75 kDa glycoprotein, named $p75^{NGFR}$, mediates low-affinity binding of any neurotrophin with similar affinity (Chao, 1994). Proteins belonging to the family of trk tyrosine kinase receptors, which interact with neurotrophins in a highly specific manner, are responsible for highaffinity binding. $p140^{trk-A}$ combines with NGF, $p140^{trk-B}$ with BDNF, and $p140^{trk-C}$ with NT-3 and NT/5 (Barbacid, 1994). Probably, each class of receptors conveys distinct signals to the target cell, since it appears that p75$^{NGFR}$ and p140$^{trk-A}$ do not form NGF-binding heterodimers (Jing et al., 1992). Interestingly, p$_{75}$$^{NGFR}$ displays structural homology to the tumor necrosis factor receptors I and II, the lymphocyte surface antigens CD30, CD40, OX40, and Fas/Apo-I surface antigen, molecules involved in preventing or mediating apoptosis (reviewed in Raffioni et al., 1993).

Since the first description of the purification of NGF from mouse maxillary gland cells, it was evident that this factor was also produced by several non-nervous cell types (Levi-Montalcini, 1987), including keratinocytes (Di Marco et al., 1993) and smooth muscle cells (Ueyama et al., 1993). Likewise, expression of the trk protooncogene has been reported by immune cells, such as monocytes (Ehrard et al., 1993a) or T lymphocytes (Ehrard et al., 1993b). It is therefore believed that neurotrophins, particularly NGF, may subserve important roles outside the nervous system.

These two lines of evidence, together with the structural homology of p75$^{NGFR}$ to a series of surface receptors, including those for cytokines, and with the observed elevated plasma levels of NGF in patients with some autoimmune diseases (Dicou et al., 1993; Bracci-Laudiero et al., 1993; L. B.-L, L. A., E. G., and G. Rasi, unpublished observation), led an investigation into whether NGF and/or its receptors were expressed by cells of the immune system. Here, it is shown that NGF is synthesized and released under basal conditions by normal human B lymphocytes, which also constitutively express both p75$^{NGFR}$ and p140$^{trk-A}$, receptor chains. In addition, endogenous NGF functions in an autocrine fashion to maintain viability of cells with the surface phenotype of memory B cells, and its neutralization in vivo abrogates a secondary humoral immune response.

Results

NGF Production By Normal Human Immunocompetent Cells

During the course of a study to assess plasma levels of NGF in various pathological settings, we noticed that particularly high amounts of cytokine were present in patients with chronic liver diseases and other autoimmune conditions. To determine which cell type, if any, amongst immunocompetent cells, was responsible for NGF production, normal peripheral blood or tonsil mononuclear cells (MNC) were fractionated into T cells, B cells, and monocytes. These cells were then cultured in the presence or absence of relevant stimuli and subsequently tested for biochemical evidence of NGF synthesis and secretion. Only B lymphocytes constitutively produced NGF and their generation of NGF was enhanced by stimulation with *Staphylococcus Aureus* of the I Cowan strain (SAC) (a). Immunoblotting demonstrated a major band in B lymphocyte conditioned medium with anti-NGF antibodies, but not with non-immune IgG (data not shown). Immunoprecipitation of metabolically labelled B cell supernatants also showed a single major band with M$_r$ 13 kDa under reducing conditions or with M$_r$ 26 kDa under non-reducing conditions, which presence was blocked by inclusion of excess unlabeled NGF. Kinetic studies of B cell lysates and supernatants showed no NGF storage pool (data not shown). In contrast to these results with B cells, no NGF production was observed with T lymphocytes or monocytes, even after stimulation. Although it has been quite recently reported that some T cell clones can produce NGF (Ehrard et al., 1993b), it appears that such cells are scarcely represented in a normal peripheral blood or tonsil sample (based on analysis of cell populations from at least twenty different donors), and B cell production therefore was focussed on.

B lymphocytes were fractionated on density gradients, and high- and low-density fractions were studied as representative of resting and in vivo activated cells, respectively. Both B cell populations produced and efficiently released NGF (the latter≈60% more than the former, data not shown). Next, resting B cells were stimulated with antibodies to the human immunoglobulin chain constant region plus Interleukin-4 (anti-$\mu$+IL-4) or with SAC, two stimuli active on B cells, the former activating surface (s) IgM$^+$ cells only, and the latter activating virtually all B lymphocytes (Romagnani et al., 1982). It was evident that anti-$\mu$+IL-4 stimulation was ineffective, while SAC greatly enhanced NGF synthesis and secretion. Analysis of supernatants of similar cultures by ELISA confirmed that anti-$\mu$+IL-4-stimulated cells and unstimulated cells gradually reduced NGF production, while SAC-stimulated cells strongly increased it. In contrast, both stimuli were effective, with respect to induction of proliferative stimulation indexes of >10 and >20, respectively. These findings indicated that SAC, but not anti-$\mu$+IL-4, triggered a metabolic pathway leading to NGF production. An alternative explanation was that lymphocytes normally responding to anti-$\mu$+IL-4, i.e., mostly virgin s$\mu^+\delta^+$ cells, did not alter NGF production (or possibly failed to produce it) following sIg cross-linking, while the lymphocytes responding to SAC, a population also comprising cells with s$\gamma^+$ or s$\alpha^+$ (s$\gamma^+$/$\alpha^+$) phenotype, did, suggesting that the cytokine was involved in functional programs specific to the latter cell type.

Expression of NGF Receptor Molecules By Normal Human Immunocompetent Cells

The observation that NGF was produced by B lymphocytes prompted a determination as to whether NGF receptors were also present, making possible an autocrine feedback loop. To this purpose, tonsil or peripheral blood T cells, B cells, and monocytes were studied for the expression of the two NGF-binding molecules that are displayed by cells in the nervous system, the p$_{140}$$^{trk-A}$ (trk) and the p75$^{NGFR}$. Western blot analyses of cell lysates using specific antibodies showed that each of the cell types studied expressed the trk molecule; interestingly, p75$^{NGFR}$ was produced by B cells only. Moreover, the same cells were studied by FACS following staining with antibodies to the p75$^{NGFR}$ chain and with Tmg 13.1, a recently described monoclonal antibody to the extracellular cytokine binding region of the trk molecule (Eager, 1991). Consistent with the immunochemical approach, double staining was observed on B cells only, while T cells and monocytes were solely stained by Tmg 13.1 (data not shown).

The simultaneous expression of both receptor chains by B lymphocytes, a situation typical of nervous cells, indicated that these cells were equipped to respond to the full range of signals conveyed by the cytokine. B cells were therefor looked at, with the goal of obtaining data relevant to the functional role of NGF in lymphocytes.

To demonstrate binding of the cytokine, and to analyze its functional effects, tonsil B lymphocytes were separated into small and large cells, and studied for their ability to bind and internalize NGF, using equilibrium binding assays. Both resting and in vivo activated B cells efficiently internalized $^{125}$I-NGF (data not shown). Observed were the saturation curves of $^{125}$I-NGF and their Scatchard transformations obtained with large and resting B cells. Large cells expressed, as expected, two classes of binding sites, demonstrating K$_d$ 30 pM (30,000 sites/cell) and K$_d$ 1 nM (10$^6$ binding sites/cell), respectively, consistent with the data reported on nervous cells. Surprisingly, when the same analysis was performed on small, resting B cells, no saturable binding could be observed, even upon incubation with very high $^{125}$I-NGF concentrations (data not shown), in spite of the evident expression of both receptor chains and the efficient internalization of the cytokine. This marked discrepancy indicated the possibility that the endogenous ligand was actually occupying the receptor sites, a situation frequently encountered when autocrine circuits are acting (Cozzolino et al., 1989; Cozzolino et al., 1990). Thus, purified small B lymphocytes were briefly (60 sec. at 4° C.) treated with culture medium buffered at pH, 3.0 and then washed with regular medium before the binding assay. Under these conditions, both high- and low-affinity $K_d$ 170 pM and 1 nM, respectively) receptors, with 90,000 and $10^6$ binding sites/cell, respectively, could be detected. To further strengthen the hypothesis that these sites were indeed occupied by NGF because of the existence of an autocrine loop, the acidic pH eluates (and the neutral pH eluates, as controls) were run in SDS-PAGE, blotted, and stained with specific anti-NGF antibodies. The cytokine was detected in the acidic eluates only. Altogether, these results confirmed the expression of two classes of fully functional NGF receptors by B lymphocytes.

Effect of Endogenous NGF Neutralization in B Lymphocytes

The above data, indicating that B cells produced NGF and expressed high- and low-affinity receptors, supported the hypothesis of an autocrine circuit. In order to understand the function exerted by this circuit, endogenous NGF was neutralized and assessed its impact on properties of B lymphocytes. To this purpose, either neutralizing antibodies to NGF were employed or, in selected experiments, NGF antisense oligonucleotides. Anti-NGF antibodies were first tested in conventional $^3$H-thymidine incorporation assays using resting peripheral blood or tonsil B lymphocytes, stimulated with anti-$\mu$+IL-4 or with SAC. Both stimuli induced a vigorous response in the presence of control pre-immune antibodies; in the presence of anti-NGF antibodies, the response to anti-$\mu$+IL-4 was unaffected, while that to SAC was diminished by 20–30% (Table 1), initially suggesting that NGF was involved in the proliferative response to SAC. However, addition of exogenous recombinant NGF failed to increase $^3$H-thymidine incorporation (Table 1), even in the presence of suboptimal doses of stimulants (data not shown), rather suggesting that the cytokine was not acting as a growth factor. Consistently, spontaneous proliferation of low density in vivo pre-activated B cells was not modulated by anti-NGF antibodies (data not shown). These stimulation experiments with anti-$\mu$+IL-4 or SAC again indicated that different cell populations were responding to the mitogens, and that they could be functionally divided on the basis of NGF utilization, in addition to NGF production. To gain support for this concept, resting tonsil B lymphocytes were separated by panning into $s\mu^+\delta^+$ cells and $s\gamma^+$ and $s\alpha^+$ cells ($s\gamma^+/\alpha^+$), which were then stimulated with SAC or anti-$\mu$+IL-4. Table 1 shows that proliferation of $s\mu^+\delta^+$ cells in response to SAC was not affected by neutralizing anti-NGF antibodies. As expected, proliferation of $s\gamma^{+/\alpha+}$ cells to anti-$s\mu$+IL-40 was very weak (data not shown), while these cells were quite responsive to SAC; when stimulation was exerted in the presence of anti-NGF antibodies, $^3$H-thymidine incorporation was reduced by >80% (p<0.0001). This finding, considered together with the results of the experiments on NGF production, suggested that the cytokine was critical for $s\gamma^+/\alpha^+$ cells and apparently dispensable for $s\mu^+\delta^+$ cells.

These data led to further exploration of the effects of NGF on resting $s\mu^+\delta^+$ cells and $s\gamma^+/\alpha^+$ cells. Taking into account that it failed to increase in vitro growth of B cells (Table 1) and in view of the known property of NGF to maintain survival of neuronal cells (in its absence those cells undergo apoptosis), considered was whether NGF might enhance survival of resting $s\mu^+\delta^+$ cells or $s\gamma^+/\alpha^+$ cells. Thus, the above populations, purified from tonsils, were cultured in the presence of anti-NGF antibodies or NGF antisense oligonucleotides for various time intervals, and the ratio of fragmented/intact DNA, as a measure of the percentage of cells undergoing apoptosis, was recorded. When $s\mu^+\delta^+$ cells were analysed, equal proportions of cells were apoptotic, both those treated with anti-NGF reagents and those with control preimmune IgG (or sense oligonucleotide). By contrast, cultures of $s\gamma^+/\alpha^+$ cells treated with anti-NGF antibodies or oligonucleotides contained >60% apoptotic cells at 60 hours, whereas control cultures had <20% apoptotic cells (p<0.0001); interestingly, the kinetics of apoptosis were much slower compared to that of $s\mu^+\delta^+$ cells, suggesting an important difference in the life potential between the latter cells and $s\gamma^+/\alpha^+$ cells in vitro.

On the whole, this set of experiments demonstrated that endogenous NGF was an autocrine survival factor for $s\gamma^+/\alpha^+$ cells, since its neutralization triggered their apoptotic death, but not for $s\mu^+\delta^+$ cells, suggesting that only the former cells could elaborate the cytokine. To test this concept, purified populations were analysed for NGF production by ELISA. It was evident that $s\gamma^+/\alpha^+$ cells produced at least eight-fold more NGF than $s\mu^+\delta^+$ cells (409 19 pg/$10^7$ cells vs 51 4 pg/$10^7$ cells; n=9).

Thus, in order to ascertain whether the functional difference between the subsets was due to utilization, rather than production, of NGF, an important determinant was investigated of the pathway leading to apoptosis, bcl-2 protein turnover (Korsmeyer, 1992). Purified resting $s\gamma^+/\alpha^+$ and $s\mu^+\delta^+$ populations were cultured with anti-NGF or control antibodies for 18 hours, and then lysed to analyze their intracellular content of bcl-2 protein. Neutralization of endogenous NGF caused the complete disappearance of bcl-2 protein from $s\gamma^+/\alpha^+$ cells, but did not affect bcl-2 protein content in $s\mu^+\delta^+$ cells, revealing major difference between the subpopulations, with respect to NGF utilization.

Anti-NGF Antibodies Deplete Memory B Cells in vivo

Since $s\mu^+\delta^+$ phenotype identifies virgin B cells, whereas cells with $s\gamma^+/\alpha^+$ phenotype comprise those lymphocytes that have already undergone the process of Ig constant region class switch, including memory B lymphocytes (Kishimoto and Hirano, 1989; Sprent, 1994), it was hypothesized that the autocrine NGF served as a survival factor for memory B cells, and decided to test this concept using an in vivo approach to analyze the well-defined hapten-specific systems Nitrophenol-BSA (NP) or Arsonate-KLH (Ars), or the complex (mosaic) antigen system Tetanus Toxoid (TT). First, it was demonstrated that a substantial identity between human and murine B cells, regarding NGF synthesis (murine $s\gamma^+/\alpha^+$ and $s\mu^+\delta^+$ cells constitutively produced 234±21 and 28±3 pg/$10^7$ cells, respectively), NGF receptor expression [murine unfractionated sIg$^+$ cells expressed≈4, 800 high-affinity ($K_d$≈135 pM) and $10^6$ low-affinity ($K_d$≈1.1 nM) binding sites per cell], and functional significance of the cytokine for cell survival in vitro ($s\gamma^+/\alpha^+$ cells presented≈70% DNA fragmentation upon exposure to neutralizing anti-NGF antibodies). Thus, groups of twenty BALB/c or C57BL/6 mice were immunized with the relevant antigen, and after 40 days a group of ten animals received a single dose of neutralizing anti-NGF IgG, while the other ten mice were injected with non-immune IgG as control. After an additional 48 hours, all animals received a recall dose of the respective antigen, and four days later all mice were sacrificed, and plasma concentrations of antigen-specific IgM and IgG were determined by ELISA. Animals receiving anti-NGF antibodies showed levels of specific IgG to the immunogen markedly lower than those of controls (p<0.001). By contrast, no difference was observed in the concentration of antigen-specific IgM, indicating that the antibody response generated by the newly formed, virgin B lymphocytes encountering the immunogen, the second "primary" response, was not affected. To further strengthen the latter conclusion, two additional groups of mice were first treated with anti-NGF IgG or with control IgG, then (48 hours later) immunized with TT, and after one week sacrificed to determine their plasma level of TT-specific IgM, which was not statistically different in the two populations (0.275±0.032 Abs 405 Arbitrary Units in treated animals vs 0.284±0.041 in controls) (data not shown).

The above findings suggested that, consistent with in vitro data, anti-NGF antibodies were able to induce cell death of most isotypically switched memory B cells, thus quenching a secondary humeral response. To obtain direct evidence supporting this concept, two groups of normal adult mice were treated with anti-NGF IgG or with control IgG, after three days spleen cells were isolated, and the proportions of B cell subpopulations were assessed by cytofluorimetry. The percentage of $s\gamma^+/\alpha^+$ cells was markedly reduced in spleens of treated mice, compared to controls, while no significant difference between the two groups was observed in the percentage of $s\mu^+\delta^+$ cells. On the whole, this set of experiments indicated that NGF also in vivo plays a role in the maintenance of memory B cells.

NGF is not a Switch Factor for B Lymphocytes

The outcome of the above in vivo NGF neutralization experiments was compatible with the hypothesis that the cytokine was an autocrine survival factor for memory B lymphocytes. However, the same results would have been observed if NGF was involved in the machinery that governs the IgMIgG class switch, along with the CD40 ligand (Aruffo et al., 1993). If so, however, a higher proportion of IgM-producing cells, together with a reduced amount of IgG- or IgA-producing cells, should be observed whenever a polyclonal population of lymphocytes is induced to differentiate in vitro in the presence of anti-NGF antibodies. Thus, normal human peripheral blood mononuclear cells were cultured for ten days with pokeweed mitogen, to stimulate polyclonal differentiation (Kishimoto and Hirano, 1989), and with either anti-NGF IgG or non-immune IgG, as negative controls, or with soluble CD40 pentamer, a genetically engineered molecule that prevents the CD40-gp39 interaction (Fanslow et al., 1992), as a positive control. Ig measurement by ELISA revealed that anti-NGF antibodies induced a definite reduction in the level of IgG and IgA in the pokeweed mitogen-stimulated cultures, but also IgM levels 20% lower than those of control cultures (Table 2). By contrast, the soluble CD40 pentamer caused a depression of IgG and IgA secretion compared to controls, and an increase in the rate of IgM secretion (Table 2).

These experiments indicated a clear difference in the mechanisms likely to be responsible for the observed changes. In fact, the soluble CD40 pentamer caused a block in the Ig class switch phenomenon, inducing an "accumulation" of cells in the pre-switch (i.e., $s^+$) compartment; in contrast, anti-NGF antibodies caused only a strong reduction of IgG- and 30 IgA-producing cells, an evidence of disappearance (death) of the respective precursors, induced by anti-NGF antibodies. These data are consistent with the results of the above in vivo experiments, whereby the reduction of $s^+$ or $s^+$ cells was not accompanied by an increase of $s^+$ cells. As a whole, these findings strongly indicated that NGF was not acting as a "switch factor" for normal human or murine B lymphocytes.

Discussion

The ability to discriminate finely among a multitude of chemical structures and to retain a trace of these encounters—specificity and memory—are the hallmarks of the immune system. While the molecular bases of specificity have been largely defined through the extensive characterization of biochemistry and genetics of the antigen receptors expressed by T and B lymphocytes, knowledge of immune memory is still largely phenomenological. In particular, it remains to be defined whether a single memory cell, like most lymphocytes, has a definite and limited life span in quiescent conditions, or else it is a long-living cell lasting for years, possibly throughout life. Several hypotheses have been proposed, the prevailing one being that the long persistence of antigen within lymphoid organs results in a continuous, slow proliferation of immune cells that maintain immunological memory (Gray, 1993). However, it is difficult to imagine how antigens can remain unmodified for years, particularly if proteinaceous (Sprent, 1994). In fact, evidence has been provided that immunological memory can be maintained for quite long periods by non-cycling cells (Schittek and Ra-jewsky, 1990), albeit the molecular mechanisms allowing their survival still are unknown. The present evidence suggests that memory B lymphocytes, when generated, may undergo the same fate of Bizzozzero "perennial" cells, whose prototype are neurons, because of their ability of producing an autocrine survival factor, NGF.

The major argument suggesting that the cytokine acts as a survival rather than as a growth factor is based on the observation that preventing NGF receptor triggering of purified $s\gamma^+/\alpha^+$ resting B cells by neutralizing anti-NGF antibodies caused massive cell death by apoptosis. In addition, when resting unfractionated B cells were stimulated with anti-$\mu$antibodies+IL4, which elicited a strong proliferative response, they did not increase NGF production rate and their proliferation was not augmented by exogenous recombinant NGF, nor was it affected by anti-NGF antibodies. Moreover, when SAC was used to stimulate the same cells, increased amounts of NGF were secreted, but further addition of exogenous cytokine failed to potentiate $^3$H-thymidine incorporation, even if suboptimal doses of stimulant were applied. Consistently, low-density in vivo pre-activated B cells expressed more NGF, but saturating doses of anti-NGF antibodies did not abolish B cell proliferation, as would be expected if the cytokine was a growth factor. Taken together, these considerations rather pointed to NGF as a survival factor.

This conclusion might appear to conflict with the reports that in the past years have suggested an intrinsic growth-stimulating activity of NGF on lymphocytes (Otten et al., 1989; Brodie and Gelfand, 1992). However, these reports can be re-interpreted taking into account that, according to these findings, addition of exogenous NGF may reduce the number of some cells spontaneously dying in vitro [particularly those originating IgA- and IgG4-secreting cells (Kimata et al., 1991)] because of low-density culture conditions, eventually leading to a higher basal proliferation in culture. Moreover, distinction between growth and survival factor may be purely nominalistic, as suggested by the observation that IL-3 and Stem Cell Factor support long-term survival of dormant non-cycling lymphohematopoietic progenitors in liquid cultures (Katayama et al., 1993).

The finding of spontaneous production of NGF by B cells lends further support to the evidence of a "phlogistic" role of NGF (Aloe et al., 1994), which probably contributes in a paracrine fashion to the function of inflammatory cells, such as macrophages, which are equipped with the receptor machinery necessary to respond to the cytokine (Ehrhard et al., 1993a), but unable to produce it (Santambrogio et al., 1994). Similar considerations apply for T lymphocytes. In this study, no attempts were made to characterize more precisely, from a phenotypic or functional standpoint, the (sub)populations of T cells expressing NGF receptors and hence probably responding to it. However, B cell-derived NGF might subserve important roles in the complex event of B cell antigen presentation to T lymphocytes, particularly when a secondary immune response has to take place. In fact, sIgG$^+$ memory B cells express receptors with the highest affinity for the antigen (Siekevitz et al., 1987; MacLennan and Gray, 1986) and are therefore privileged in the competition for binding that occurs when the antigen is in limited amounts. Their ability to release NGF might be essential for a proper activation of either memory or naive T cells.

An important point that has emerged from this study is the simultaneous expression of both chains known to bind NGF—the trk molecule and the p75$^{NGFR}$ molecule—by B lymphocytes, a feature typically presented by neuronal cells. Although NGF was the first cytokine to be characterized, still relatively little is known about the specific metabolic pathways triggered by its interaction with either receptor chain, nor is it clear whether or not both chains cooperate in binding a single molecule of ligand, as conflicting results on this topic have been reported (Jing et al., 1992; Benedetti et al., 1993; Huber and Chao, 1995). However, it has been shown that expression of p$_{75}^{NGFR}$ induced neural cell death constitutively when the protein was unbound, while its binding by NGF or by monoclonal antibodies inhibited cell death (Rabizadeh et al., 1993), suggesting that it is per se able to transmit a biological signal, consistent with the structural homology between p$_{75}^{NGFR}$ and a series of receptor chains, including TNFRI, TNFRII, Fas/Apo-1, and CD40, all involved in inducing or preventing apoptosis in target cells (reviewed in Raffioni et al., 1993). These latter data are entirely in accord with the finding that neutralization of the autocrine NGF, but not treatment with anti-p75$^{NGFR}$, determines B cell death (manuscript in preparation), pointing to this receptor chain as a mediator of signals acting upon the survival/death divide. Interestingly, in spite of the structural homology between p75$^{NGFR}$ and CD40, it was clear that NGF does not take part in the Ig class switch process.

In some cell types, such as keratinocytes or melanocytes (Yaar et al., 1994; Di Marco et al., 1993), trk mediates signals which potentially stimulate cell proliferation, in contrast to what occurs in neuronal cells, whereby NGF prevents apoptosis following trk engagement, possibly via phosphatidyl inositol-3 kinase activation (Yao and Cooper, 1995). This discrepancy might be solved by the existence of other chain(s), that may participate in the formation of a multi chain receptor complex with trk and/or p75$^{NGFR}$, as usually occurs for most cytokine receptors. The latter hypothesis would also explain the limited but significant difference we observed in NGF binding affinities displayed by large and resting B cell populations ($\approx$30 pM vs$\approx$170 pM, respectively).

Separation of normal resting B lymphocytes on the basis of surface Ig isotype expression identifies two functionally different subpopulations, i.e., s$\mu^+\delta^+$ virgin and s$\gamma^+$/$\alpha^+$ memory cells (Kishimoto and Hirano, 1989). We used this approach to get insights into the role of NGF autocrine circuit and observed several features which led to the idea that the cytokine is an endogenous survival factor for memory cells, both in humans and in mice. First, while both virgin and memory cells expressed basically the same levels of NGF receptors, the latter produced at least eight-fold more NGF protein than the former. Second, treatment with neutralizing anti-NGF antibodies induced disappearance of bcl-2 protein and, consistently, massive DNA fragmentation in s$\gamma^+$/$\alpha^+$ cells, while it was insignificant for s$\mu^+\delta^+$ cells. Third, in vivo administration of anti-NGF antibodies abolished secondary antigen-specific immune responses, but failed to affect the primary IgM response. Finally, a single injection of anti-NGF antibodies to normal animals caused a marked reduction in the percentage of isotypically switched B lymphocytes, which comprise memory cells. On the other hand, these findings raise at least two important issues, namely the maturational stage at which NGF gene expression takes place and the relationships between NGF and bcl-2.

The low but detectable production of NGF by s$\mu^+\iota^+$ cells would indicate a relatively early onset during B cell ontogeny, whose functional significance should be further elucidated. However, based on quantitative considerations about the magnitudes of different B cell subpopulations, it is suggested that s$\mu^+$ cells also comprise memory lymphocytes, able to originate cells secreting Ig other than IgM (Gray, 1993). If so, the s$\mu^+$ cell-derived NGF we observed could be produced by the latter cells and, in this case, NGF gene expression might be linked to, and possibly regulated by, the same molecular mechanisms operating the Ig class switch.

Little is presently known on the molecular pathways that relate NGF receptor chains with bcl-2, a protein critically regulating survival both in neurons and in lymphoid cells, particularly in memory B cells (Batistatou a et al., 1993; Hawkins and Vaux, 1994; Nunez et al., 1991), which in fact disappears from resting sIgG$^+$ or sIgA$^+$ cells treated with neutralizing anti-NGF antibodies. Recently, evidence has been provided that reactive oxygen species and, more generally, alterations in the cellular redox potential may be involved (Greenlund et al., 1995). In this connection, it has been shown that low-rate nitric oxide production in EBV-infected B lymphocytes, constitutively expressing nitric oxide synthase, prevents apoptosis (Mannick et al., 1994), probably acting at multiple levels on thiol-sensitive pathways that also regulate metabolism of bcl-2, susceptible to intracellular redox potential and participating in its maintainance (Hockenbery et al., 1993). Interestingly, Mosialos et al. (1995) quite recently showed that functional relationships exist among the proteins that transduce signals from the TNF/Fas/NGF receptor family; since TNF induces alterations in cellular redox equilibrium (Ishii et al., 1992), these molecules could also participate in the adaptive response elicited by NGF. We are presently investigating the latter hypothesis in memory B cells following NGF neutralization.

One striking piece of evidence deserving consideration is the observation that, in lymphoid cells at least, both apoptosis and cell survival are regulated through autocrine circuits, the former involving Fas/Apo-1 and its ligand (Brunner et al., 1995; Dhein et al., 1995; Ju et al., 1995), the latter involving NGF, according to our data. Such an arrangement ensures that all the molecular requirements needed to commit the cell to either pathway are immediately available, and helps to understand how lymphoid organs are sites in which complex functional changes may occur in an ordered manner. The evidence that the autocrine circuit is public—involving secretion of ligands and binding to extracellular receptors, instead of being private or intracrine—strongly suggests that function of both systems may be modulated by either receptor antagonists or soluble receptors, originating a complex network of "social" controls over the fate of a single lymphocyte. Interestingly, the latter complexity may yield several opportunities to interefere with such dynamics using pharmacological approaches.

Experimental Procedures

Cell Isolation and Culture

Human T lymphocytes were separated from peripheral blood mononuclear cells or from tonsil cells by E-rosetting. Monocytes were isolated by adherence on plastic Petri dishes. B lymphocytes were further purified from the non-T population using CD19-coated magnetic beads. Murine B lymphocytes, depleted of monocytes as above, were isolated from spleens by two rounds of negative selection using an anti-CD3ε monoclonal antibody (Boheringer Mannheim, Milano, Italy). The purity of population was more than 95%, as assessed by flow cytometry. Human or murine B cells were further fractionated into resting (high-density) and activated (low-density) cells by Percoll density gradients. The proportions of sIgM+, sIgG+, and sIgA+ cells in tonsil resting B cells were typically 65%, 25%, and 10%, respectively, as assessed by flow cytometry.

For proliferation assays, B cells were cultured in 96-well plates at the concentration of $10^6$/ml in RPMI 1640 medium (GIBCO, Milano), supplemented with 10% v/v foetal calf serum (FCS, Hyclone, Logan, Utah), for 72 hours in humified air with 5% $CO_2$. Heat-inactivated *Staphylococcus Aureus* of the I Cowan strain (SAC, Boheringer Mannheim) was used at the final dilution of 1:10,000. Human rIL-4 (R&D, Minneapolis, Minn.) was used at 100 U/ml, rabbit anti human-chain was used at 1 g/ml, NGF (Boheringer Mannheim) was used at 100 ng/ml, neutralizing goat anti-NGF antibodies [R&D, $ND_{50}$=10 μg/ml in the IMR-32 neuroblastoma cell proliferation assay (Janet et al., 1995) in response to 100 ng/ml of NGF] or pre-immune goat IgG were used at 10 μg/ml. Cells were pulsed with 0.5 Ci of $^3$H-thymidine in the last 12 hours of culture and counted in a β-scintillation counter.

For immunoglobulin production, human peripheral blood mononuclear cells were cultured for 12 days, in the presence or absence of pokeweed mitogen (GIBCO), 10 g/ml, anti-NGF antibodies (10 g/ml), pre-immune goat IgG (10 g/ml), CD40- or CD4-supernatant (1:1 0 final dilution). Supernatants were collected and tested for IgG, IgA, IgM production by ELISA.

For analysis of NGF production, cells ($2 \times 10^7$) were cultured at $10^7$/ml in serum-free RPMI-1640, supplemented with 10% (v/v) Nutridoma (Sigma) for different times in the presence or absence of SAC (1:10,000 final dilution), phytohemoagglutinin (PHA-P, 1 g/ml, GIBCO), lipopolysaccharide (LPS, 10 g/ml, Sigma), and supernatants assayed by ELISA.

B cell subpopulations were isolated by panning procedures using plastic Petri dishes coated with rabbit anti-human IgM and rabbit anti-human IgD (referred to as sμ+δ+), or rabbit anti-human IgG plus rabbit anti-human IgA (referred to as s+/+), or goat anti-mouse IgM and IgD or IgG and IgA, prepared as described (Wysocki et al, 1978). The purity of the isolated population was always >90%, as assessed by flow cytometry using specific mAbs. In order to rule out the interference of the activation process following sIg receptor triggering, all the experiments were repeated using the reciprocal non-adherent populations (e.g., s− cells, mostly comprising s+/+ cells), recovered after three rounds of adherence from Ig-coated plates.

Determination of Cell Viability and DNA Fragmentation

Human and murine B cell subpopulations, cultured at $5 \times 10^6$/ml with 10 μg/ml anti-NGF IgG or pre-immune IgG, or with 20 μM 18-mer antisense or sense oligonucleotides complementary to the nucleotides 54–72 of the NGF coding region (Primm, Milano, Italy), were diluted 1:1.5 with 5 mM Tris, 20 mM EDTA, and 0.5% (v/v) Triton X-100, pH 8.0, and allowed to lyse for 15 min on ice before centrifugation for 20 min at 27,000×g, to separate intact chromatin (pellet) from DNA fragments (supernatant). Pellets were resuspended in 5 ml of a buffer containing 10 mM Tris and 1 mM EDTA, pH 8.0, and pellet and supernatant samples were assayed for DNA content, using the diphenylamine reagent (1.5% diphenylamine in acetic acid plus 10% acetaldehyde) for 16 hr at 30° C. (Burton, 1956). The optical density at 600 nm was measured for each sample. Percentage of DNA fragmentation was calculated according to McConkey et al. (1989) Cell viability was evaluated by trypan blue dye exclusion.

Radioligand Binding Studies

For analysis of surface NGF receptors, human resting tonsil or murine splenic B lymphocytes were acid-treated with RPMI-1640 medium buffered at pH 3.0 for 1 min on ice and washed with PBS. Acid-treated resting B lymphocytes and in vivo activated large B lymphocytes phocytes were then incubated at $10^6$/ml with different concentrations of $^{125}$I-NGF (Amersham, Milano, specific activity 50 Ci/g), in the presence or absence of excess unlabelled human rNGF for 2 hours at 4° C. Cells were washed and bound radioactivity was counted in aγ-counter. Specific binding was calculated for each experimental point and data were analysed by a scientific program (FIG. P, Biosoft, Cambridge, UK). For radioligand internalization, cells were cultured as above with 0.5 nM $^{125}$I-NGF in the presence or absence of excess unlabelled NGF, washed and cultured at 37° C. for 2 hours, then treated with glycin buffer (pH 2.8) and lysed. Membrane-bound (acidic eluate) and cell associated radioactivity were determined by counting in aγ-counter. The neutral pH wash and the acidic pH eluate from $10^8$ resting B cells was TCA-concentrated, blotted on nitrocellulose, and immunostained with anti-NGF IgG or with pre-immune IgG for detection of the receptor-bound endogenous ligand.

Immunochemical Analysis

For western blot analysis, supernatants or NP-40 (0.25% in PBS) lysates of $2 \times 10^7$ cells were TCA-precipitated, washed with ethanol and diluted 1:1 in 2-mercaptoethanol Laemmli buffer. Samples were run in SDS-PAGE, blotted against nitrocellulose filters and immunostained with the appropriate antibodies [goat anti-NGF, rabbit anti-trk (Genzyme, Boston, Mass.), mouse anti-p75$^{NGFR}$ (Boheringer Mannheim), mouse anti-bcl-2 (Santa Cruz Technology, Milano)] or with pre-immune Ig. The antigen-antibody complexes were visualized using appropriate secondary antibodies and the ECL detection system, as recommended by the manufacturer (Amersham). For endogenous labeling and immunoprecipitation studies cells were washed three times with cystein-free RPMI-1640 (GTBCO) and cultured at $10^7$/ml in the same medium supplemented 5% dialysed FCS and 200 Ci of $^{35}$S-cystein (Amersham, specific activity 800 Ci/mM) for 4 hours at 37° C. in 5% $CO_2$. Supernatants were removed, and cells were washed in cold PBS and lysed in 0.25% NP-40 plus 1 mM PMSF. Supernatants and cell lysates were immunoprecipitated as described (Cozzolino et al., 1990), in the presence or absence of 100 μg/ml of human rNGF. The immunoprecipitates were washed, eluted in SDS Laemmli buffer, with or without 2-mercaptoethanol, and run on 15% SDS-PAGE slabs, which were treated with Amplify (Amersham), dried and exposed to Hyper film MP (Amersham) at −70° C.

Mice Immunization and Treatment

Ars-KLH was prepared by diazoting p-aminophenylarsonic acid and coupling to keyhole limpet hemocianin (KLH, Calbiochem) in a ratio of 40 mg of hapten to 1 g of protein (Nisonoff, 1967). (4-Hydroxy-5-iodo-3-nitro-phenyl)acetyl (NIP, a generous gift of Dr. D. Schilovich, HSR, Milano) was coupled to bovine serum albumin NIP-BSA) according to Reth et al, 1978. Two groups of twenty female Balb/c mice, 6 weeks old, were injected s.c. in the neek with 0.1 ml of TT solution [15 μg/ml (Anatetal, Biocine-Sclavo, Siena, Italy)] or i.p. with Ars-KLH (0.1 mg), and a group of twenty C57BL/6 mice was immunized i.p. with 0.1 mg NIP-BSA. Forty days after priming, ten mice of each group were treated with goat anti-NGF IgG (500 g/mouse), the other with pre-immune goat IgG (500 g/mouse), and 48 hours later all mice were boosted with the same dose of the relevant antigen. Four days after the second immunization, blood was withdrawn from the retroorbital venus plexus. Other groups of ten mice immunized with TT, NIP-BSA, or Ars-KLH were used for the measurement of antigen-specific IgG immediately before the boost injection.

For FACS analysis of splenocytes, groups of ten adult BALB/c mice were treated with two injections in 72 hours (0.5 mg/mouse) of anti-NGF antibodies or goat IgG. After an additional 72 hours, mice were sacrificed and splenocytes, depleted of monocytes, were obtained. Percentage of surface $IgG^+$, $IgA^+$, or $IgM^+$ splenocytes was determined by cytofluorimetry using specific antibodies.

ELISA

NGF ELISA was performed as described by Söderstrom et al. (1990). For evaluation of Tetanus Toxoid (TT)-specific IgG or IgM titer, plates were coated with 50 l of TT (10 g/ml) in 0.1 M borate buffer, pH 8.6, overnight at 4° C. For evaluation of NIP or Ars-specific IgG or IgM titer, plates were coated with NIP-KLH or Ars-BSA (35 μg/ml in PBS). Specific IgG and IgM titer to the immunizing complexes were also evaluated by coating the plates with NIP-BSA or Ars-KLH. After saturation with PBS containing 1% BSA and rinsing with PBS with 0.05% (v/v) Tween 20, coated wells were incubated for 1 hour at 37° C. with serial dilution of mouse sera; a pool of pre-immune mouse sera was used as negative control. Bound Ig were detected by addition of alkaline phosphatase-conjugated goat anti-mouse IgG or IgM. The final reaction was visualized by incubating with NPP (Sigma) substrate solution, and absorbance at 405 nm was recorded.

TABLE 1

Effect of anti-NGF antibodies on mitogen-induced proliferation of resting B lymphocytes

| | $^3$H-thymidine incorporation (cpm) | | |
|---|---|---|---|
| | Exp. 1 | Exp. 2 | Exp. 3 |
| UF B cells | 251 | 240 | 306 |
| UF B cells + NGF | 305 | 312 | 403 |
| UF B cells + SAC | 13,808 | 32,010 | 17,040 |
| UF B cells + SAC + anti-NGF | 11,488 | 25,432 | 13,050 |
| UF B cells + SAC + goat IgG | 13,765 | 32,456 | 17,321 |
| UF B cells + SAC + NGF | 14,056 | 34,021 | 19,028 |
| UF B cells + IL-4 + anti-μ | 12,896 | 15,675 | 11,366 |
| UF B cells + IL-4 + anti-μ + anti-NGF | 12,798 | 15,254 | 10,987 |
| UF B cells + IL-4 + anti-μ + goat IgG | 12,913 | 16,070 | 11,654 |
| UF B cells + IL-4 + anti-μ + NGF | 13,004 | 16,876 | 12,114 |
| Purified $sμ^+δ^+$ cells | 384 | 426 | 368 |
| Purified $sμ^+δ^+$ cells + SAC + goat IgG | 6,863 | 7,121 | 7,256 |
| Purified $sμ^+δ^+$ cells + SAC + anti-NGF | 6,943 | 6,889 | 7,124 |
| Purified $sγ^+/α^+$ cells | 279 | 344 | 368 |
| Purified $s^{γ+}/α^+$ cells + SAC + goat IgG | 13,935 | 14,759 | 13,157 |
| Purified $s^{γ+}/α^+$ cells + SAC + anti-NGF | 2,468 | 3,137 | 2,324 |

Resting unfractionated (UF) B lymphocytes or the indicated purified populations were cultured for 48 hours and pulsed with $^3$H-thymidine in the last 12 hours. Data are expressed as mean $^3$H-thymidine incorporation of triplicate cultures. SD was always less than 10%. SAC was used at the final dilution of 1:10,000. Goat anti-NGF antibodies or pre-immune goat IgG were used at the concentration of 10 g/ml. Recombinant human NGF was used at the concentration of 100 ng/ml. IL-4 was used at the concentration of 100 U/ml. Polyclonal rabbit anti- was used at the concentration of 1 g/ml.

TABLE 2

Effect of anti-NGF antibodies on Ig production by PWM-stimulated PBMNC

| | Ig (ng/ml) | | |
|---|---|---|---|
| | IgM | IgG | IgA |
| Medium alone | 84 | 30 | 676 |
| PWM | 1,028 | 966 | 10,716 |
| PWM + a-NGF | 674 | 374 | 1,350 |
| PWM + goat IgG | 987 | 995 | 9,243 |
| PWM + CD40μ | 1,530 | 554 | 4,794 |
| PWM + CD4μ | 928 | 1,024 | 9,865 |

Human PBMNC were cultured at $3 \times 10^6$ cells/ml for 12 days in the presence or absence of PWM (10 g/ml), goat anti-NGF antibodies or pre-immune goat IgG (10 g/ml), CD40 or CD4 supernatant (1:10 final dilution). At the end of the incubation, supernatants were collected and IgA, IgG, IgM were measured by ELISA using specific antibodies. Data are expressed as mean Ig concentration of triplicate wells; SD was <15%.

EXAMPLE 3

The age-associated changes in humoral immunity affect the quality more than the quantity of the antibody response. Changes in the quality of the antibody response with age include shifts in antibody isotypes from IgG to IgM and in antibody affinities from high to low. The impaired responses of the elderly to most vaccines and the greater susceptibility of the elderly to infections has fostered a view that immune senescence leads to a state of immune deficiency. Although these changes can be largely traced to an impaired capacity of T cells to facilitate the maturation of B cells with respect to isotype and affinity maturation in the perifery, this example shows an impaired capacity of memory B cells from elderly animals to survive, due to an impaired production of NGF. NGF administration during the maturation phase of memory B cells restores the specific, high-affinity IgG production in aged mice immunized with a commonly used hapten, NIP-BSA.

Results and Discussion

Specific IgG Production is Profoundly Depressed in Aged Mice Immunized with NIP

Figure 3:
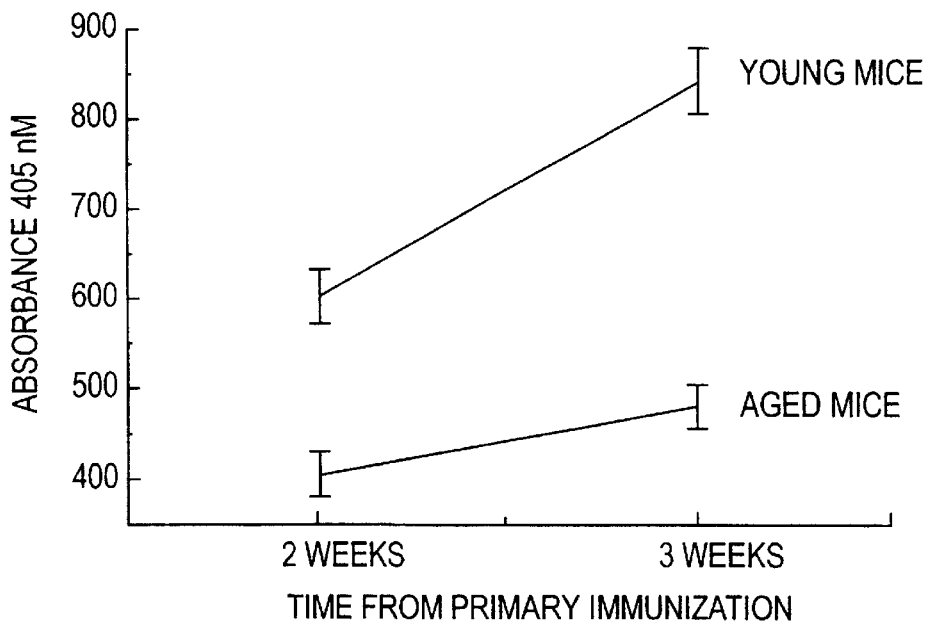
FIG. 3 is a graph showing antibody production in young and aged mice.

One group often aged (>5 months old) and one group of ten young (≦8 weeks old) C57/BL6 female mice were immunized i.p. with 0.1 mg per mouse of (4-hydroxy-5-iodo-3-nitro-phenyl)acetyl-bovine serum albumin (NIP-BSA) (Reth et al, 1978) in 0.1 ml phosphate-buffered saline (PBS), resuspended in 0.1 ml complete Freund's adjuvant. After 21 days, 0.4 ml of blood were obtained from each animal by retro-orbital plexus aspiration, and the anti-BSA antibodies were neutralized by addition of BSA to the serum samples. NIP-specific IgG and IgM titer was then assessed in ELISA. FIG. 3 shows that the specific IgG response against NIP was significantly affected in aged mice compared to young mice, while the specific IgM response against the hapten was similar in the two groups of mice. These results suggest that the mechanisms underlying the production of NIP-specific high-affinity immunoglobulin (somatic hypermutation, isotypic switch) are defective in aged mice.

It has been reported that NGF is an autocrine survival factor for memory B lymphocytes (Torcia et al., 1996). In order to study whether or not the defective immune response of aged mice could be attributed to a massive death of memory B cells, induced by the absence of NGF production or NGF availability, we isolated memory B cells (as sIgD⁻ lymphocytes) by panning techniques from the spleen of 10 aged mice and from 10 young mice as control. The cells were cultured for 16 hours at 37° C., the supernatants were harvested, and NGF was measured by ELISA techniques. Table 3 shows that memory B cells isolated from aged mice are unable to produce NGF, while the same population, isolated from young mice, produce high levels of the cytokine, as reported (Torcia et al., 1996).

TABLE 3

NGF production by sIgD⁻ splenocytes from old or young mice

| | Unstimulated production of NGF (pg/ml) |
|---|---|
| old mice | <9 |
| young mice | 535.3 ± 43.1 |

As a consequence of impaired NGF production, the survival curve of memory b cells from aged mice was consistently shorter, if compared to that of the same population isolated from young mice.

What is claimed is:

1. A pharmaceutical combination for enhancing vaccine effectiveness in immunodeficient animals, comprising:
    A) an immune response-triggering vaccine capable of stimulating production in an animal of antibodies to a disease-causing agent foreign to said animal; and
    B) a vaccine effectiveness-enhancing amount of Nerve Growth Factor (NGF), which enhances production of said antibodies in said animal, in response to said vaccine;
    C) wherein said animal is an immunodeficient animal, and wherein said vaccine and said NGF can be administered separately or together.

2. The pharmaceutical combination of claim 1, wherein said vaccine is in an amount of from about $1 \times 10^{-9}$ g to about $1 \times 10^{-3}$ g, and said NGF is in an amount of about 0.001–100 mg/kg.

3. The pharmaceutical combination of claim 1, wherein said vaccine is in an amount of from about $1 \times 10^{-8}$ g to about $1 \times 10^{-4}$ g, and said NGF is in an amount of about 0.1–10 mg/kg.

4. The pharmaceutical combination of claim 1, wherein said NGF is in an amount of about 0.3–3 mg/kg.

5. The pharmaceutical combination of claim 1, comprising a composition including said vaccine and said NGF.

6. The pharmaceutical combination of claim 5, wherein said composition includes a pharmaceutically acceptable carrier.

7. A vaccination method comprising administering to an immunodeficient animal a pharmaceutical combination for enhancing vaccine effectiveness, said pharmaceutical combination comprising:
    A) an immune response-triggering vaccine capable of stimulating production in an animal of antibodies to a disease-causing agent foreign to said animal; and
    B) a vaccine effectiveness-enhancing amount of Nerve Growth Factor (NGF), which enhances production of said antibodies in said animal, in response to said vaccine;
    C) wherein said animal is an immunodeficient animal, wherein said vaccine and said NGF can be administered separately or together, and wherein effectiveness of said vaccine in said animal is enhanced by said NGF.

8. The method of claim 7, wherein said animal is human, and said vaccine is selected from the group consisting of Influenza vaccine, Hemophilus influenzae vaccine, Hepatitis A virus vaccine, Hepatitis B virus vaccine, Hepatitis C virus vaccine, Tuberculosis vaccine, Herpes-Zoster virus vaccine, Cytomegalovirus vaccine, Pneumococcal pneumonia vaccine, Meningococcal meningitis vaccine, Diphtheria vaccine, Tetanus vaccine, Rabies vaccine, *Helicobacter pylori* vaccine, polio vaccine and smallpox vaccine.

9. The method of claim 7, wherein said vaccine is in an amount of from about $1 \times 10^{-9}$ g to about $1 \times 10^{-3}$ g, and said NGF is in an amount of about 0.001–100 mg/kg.

10. The method of claim 7, wherein said vaccine is in an amount of from about $1 \times 10^{-8}$ g to about $1 \times 10^{-4}$ g, and said NGF is in an amount of from about 0.1–10 mg/kg.

11. The method of claim 7, wherein said NGF is in an amount of about 0.3–3 mg/kg.

12. The method of claim 7, wherein said vaccine is administered as a booster dose of vaccine.

13. The method of claim 12, wherein said NGF is administered about 3–4 days prior to said booster dose of vaccine.

14. The method of claim 12, wherein said NGF also is administered substantially concurrently with administration of said vaccine.

15. The method of claim 7, wherein said vaccine and said NGF are administered by injection.

16. A vaccination method comprising:
    administering to an immunodeficient animal a first dose of an immune response-triggering vaccine capable of stimulating production in an animal of antibodies to a disease-causing agent foreign to said animal;
    then, within a time period of between about 1 week and about 2 months after administration of said first dose, administering to said animal either 1) a vaccine effectiveness-enchancing amount of Nerve Growth Factor (NGF) which enhances production of said antibodies in said animal in response to said vaccine or 2) booster dose of said vaccine, along with a vaccine effectiveness-enhancing amount of said Nerve Growth Factor (NGF), so as to enhance effectiveness of said vaccine in said animal.

17. The method of claim 16 wherein said time period is about 10–45 days.

18. The method of claim 16 wherein said time period is about 10–30 days.

19. The method of claim 16 wherein said time period is about 10–20 days.

* * * * *